United States Patent [19]
Hirata

[11] Patent Number: 5,643,300
[45] Date of Patent: Jul. 1, 1997

[54] EARDRUM UNDERSURFACE SCRAPER

[76] Inventor: Keisuke Hirata, 1920-1, Noginomori-cho 4-chome, Ogaki-shi Gifu-ken 503, Japan

[21] Appl. No.: 453,868

[22] Filed: May 30, 1995

Related U.S. Application Data

[62] Division of Ser. No. 177,403, Jan. 5, 1994, Pat. No. 5,501,700.

[30] Foreign Application Priority Data

Jan. 8, 1993 [JP] Japan ......................... 5-32387

[51] Int. Cl.⁶ ............................ A61B 17/32; A61B 10/00
[52] U.S. Cl. ........................ 606/167; 606/170; 128/757
[58] Field of Search ........................ 606/160, 167, 606/170; 128/757

[56] References Cited

U.S. PATENT DOCUMENTS

| | | | |
|---|---|---|---|
| 584,407 | 6/1897 | SaintCyr, Jr. | 606/160 |
| 667,726 | 2/1901 | McDade | 606/160 |
| 839,641 | 12/1906 | Rearley | 606/160 |
| 2,437,329 | 3/1948 | Moore | 128/757 |
| 4,854,316 | 8/1989 | Davis . | |
| 5,061,272 | 10/1991 | Reese | 128/757 |
| 5,236,455 | 8/1993 | Wilk et al. . | |
| 5,246,455 | 9/1993 | Shikani . | |
| 5,250,061 | 10/1993 | Michelson | 606/160 |
| 5,254,133 | 10/1993 | Seid . | |
| 5,282,827 | 2/1994 | Kensey et al. . | |
| 5,334,217 | 8/1994 | Das . | |
| 5,342,393 | 8/1994 | Stack . | |
| 5,348,023 | 9/1994 | McLucas | 128/757 |

FOREIGN PATENT DOCUMENTS

| | | |
|---|---|---|
| 399782 | 11/1990 | European Pat. Off. . |
| 2627079 | 2/1988 | France . |
| 150428 | 9/1981 | Germany . |
| 2422383 | 12/1982 | Germany . |
| 1217363 | 3/1986 | U.S.S.R. . |
| 1526662 | 12/1989 | U.S.S.R. . |
| 92/08415 | 5/1992 | WIPO . |
| 93/05720 | 4/1993 | WIPO . |
| 93/20765 | 10/1993 | WIPO . |

OTHER PUBLICATIONS

Tympanoplasty: Atlas of Ear Surgery ed. by W.H. Saunders, M.M. Paparella, A.W. Miglets, 1980 pp. 348–349.

R. Yuasa, M. Suetake, Y. Kaneko, J. Kambayashi "A New Simple Myringoplasty with Fibrin Glue" Transplants and Implants in Otology pp. 207–210 Proceedings and Implants in Otology 1991, N. Yanagisawa, J. Suzuki, Kugler Pub. NY 1992.

H. Naganuma, T. Shitara, K. Tokumasu, M. Okamoto, M. Hirayama: "Myringoplasty Using a Temporal Fascia Homograft" Otology Japan, vol. I (5), pp. 44–48, 1991.

*Primary Examiner*—Michael Buiz
*Assistant Examiner*—Nancy Mulcare
*Attorney, Agent, or Firm*—Birch, Stewart, Kolasch & Birch, LLP

[57] ABSTRACT

An eardrum perforation patch and an eardrum undersurface scraper for application of the patch. The eardrum perforation patch comprises double plates connected together with a coupler and these elements are made of artificial material. The plates comprise a supporting piece and a closure piece. After being inserted into the tympanic perforation the closure piece pinches the perforation margin and it stays steadily in place until it changes to a new part of the tympanic membrane. The eardrum undersurface scraper comprises a shaft, a neck and a head with a blade edge. The neck is curved at an angle of more than 90 degrees, twisted and rotated, so that the blade edge gains access to target points behind the tympanic membrane and scrapes and entirely rakes out the mucosal barrier on the undersurface grafting bed of the tympanic membrane through the tympanic perforation. The combination of the eardrum perforation patch and the eardrum undersurface scraper is useful in repairing the tympanic perforation.

9 Claims, 6 Drawing Sheets

EARDRUM UNDERSURFACE SCRAPER

This application is a divisional of application Ser. No. 08/177,403, filed on Jan. 5, 1994, now U.S. Pat. No. 5,501,700, the entire contents of which are hereby incorporated by reference.

FIELD OF THE INVENTION

The invention relates to a patch for repair of an eardrum perforation, and an oto-surgical tool to provide a transplantation bed in the undersurface of the eardrum for grafting the patch.

DESCRIPTION OF THE BACKGROUND ART

One method for treatment of a tympanic perforation uses a graft patch which is placed on the undersurface of the tympanic membrane after introducing the patch through the perforation. This grafting method belongs to the group of undersurface techniques. Because this surgical method is always performed through the external ear canal and the tympanic perforation, it minimizes surgical invasion and therefore is preferable. The grafting material of the patch in conventional methods is usually made of living human tissue, for example, temporalis fascia or subcutaneous connective tissue which is taken from the patient through an incision in his or her scalp during the operation.

In preparation of the tympanic membrane remnant for grafting, trimming of the perforation margin is performed by using a pick and a tiny cup forceps, and otherwise scoring is performed on the undersurface of the remnant membrane by inserting the head of a very tiny sharp-spoon, the tip of an angled pick or the tip of a curved injection needle through the perforation.

In order to fix the graft close to the undersurface of the tympanic membrane remnant, some gelatin sponge is packed in the tympanic cavity to support the graft temporally, or some fibrin glue is applied so that the graft adheres to the tympanic membrane remnant.

Generally speaking, a grafting technique should minimize its harm to the patient's body. In some prior methods, grafting material is obtained by making a new incision in some other area of the patient's body. This incision gives the patient additional pain and injury.

On the other hand, if artificial material, for example, lyophyrized dura as collagen fiber membrane is used, it increases the possibility of postoperative detachment because of its lack of vascularity. This usually results, in the whole graft falling off, or slit formation and subsequent graft failure. Therefore, it is hard to expect success of perforation closure with artificial grafting material.

For good blood circulation and to promote growth of fibroblast and capillary vessels in the graft, the contact of the graft with the vascular bed should be direct, tight and stable.

If absorbable gelatin sponge is packed in the tympanic cavity in order to support the graft temporally, the gelatin sponge irritates the mucosal lining of the tympanic cavity and induces hypersecretion and infection and otorrhea are apt to occur. The packing also interrupts immediate improvement of hearing after the operation as well.

If fibrin glue is used as an adhesive medium, supporting means is largely free of these problems. But the glue itself is apt to be dissolved by secretion in the tympanic cavity in the healing process. This brings about a loss of contact of the graft with the tympanic membrane remnant and often results in falling off of the graft.

There should also be a good blood supply to keep the reconstructed component viable. This requires that the mucosa at the back of the fibrous lamina propria around the perforation be entirely removed to provide a vascular bed for the undersurface grafting.

But trimming of the margin around the tympanic perforation cannot provide any suitable vascular bed, and, to make matters worse, it gets the perforation larger and increase the time of postoperative healing.

Scoring undersurface around the perforation removes the mucosal layer only partially in lines. Therefore, the graft cannot directly contact the vascular bed because of mucosal barrier. The fibroblast and capillary vessels can hardly enter into the collagen fiber network of the graft as a result.

Those are some of the inherent problems in the prior undersurface techniques and they lead to graft failure in eardrum perforation repair.

SUMMARY OF THE INVENTION

The purpose of the present invention is to solve these serious problems in the conventional techniques for eardrum perforation repair as mentioned above, and to provide an eardrum perforation patch and an eardrum undersurface scraper to conveniently close the tympanic perforation using artificial material instead of living human tissue with a high success rate.

That is, an eardrum perforation patch of the present invention is characterized in that it comprises double plates connected together with a coupler and these elements are made of artificial material. After being inserted into the tympanic perforation, the plates pinch the perforation margin and will therefore stay in place steadily until at least the inner plate changes to a new part of the tympanic membrane.

An eardrum undersurface scraper of the present invention is characterized in that it has a neck which is curved, twisted and/or rotated, so that its blade edge gains access to target points behind the tympanic membrane. The blade edge scrapes and entirely rakes out the mucosal layer on the undersurface around the perforation margin only through the tympanic perforation in order to prepare a grafting bed for the patch with sufficient vascularity for promoting new vasculization of the eardrum perforation patch.

The present perforation patch has a benefit of not requiring living human tissue as grafting material. It therefore avoids unnecessary incision and harmful pain to the patient.

The eardrum perforation patch of the present invention also needs neither packing in the tympanic cavity for support nor adhesive medium. The contact of the graft with the vascular bed is stable, and the hearing loss due to the perforation decreases immediately after the operation.

The eardrum undersurface scraper has another benefit in that it entirely removes mucosal layer on the undersurface of the tympanic membrane and exposes a vascular bed as a grafting bed only through the tympanic perforation. The tympanic membrane remnant need neither be elevated nor be incised for visualization of the undersurface of the eardrum at all. All existing useful skin layer and lamina propria are preserved.

Furthermore, the present invention either eliminates or greatly diminishes all of the above problems of the conventional undersurface tympanoplasty techniques through the tympanic perforation. This invention is therefore simple, safe, reasonable and yields a high degree of success.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

First, the details of the present invention are described about eardrum perforation patches, and second, about eardrum undersurface scrapers separately.

The eardrum perforation patch comprises a closure piece 1, at least one coupler 2 and a supporting piece 3 as shown in FIGS. 1–4. The closure piece 1 and the supporting piece 3 are shaped as a disc and sutured with a traction thread as the coupler 2. The closure piece 1 and supporting piece 3 are parallel with a narrow gap therebetween. The closure piece 1 and the supporting piece 3 have the same diameter with 1 to 2 mm. overlap around the entire circumference of the tympanic perforation to be closed.

The closure piece 1 is made of an absorbable artificial material with biological affinity for living tissue such as collagen fiber membrane, for example, lyophyrized human dura. The supporting piece 3 is made of the same material as the closure piece 1 or less absorbable material, for example, chitinous fiber membrane. The traction thread as the coupler 2 is made of surgical suture thread which is absorbable by living tissue.

When the tympanic perforation is small, the supporting piece 3 can be omitted. Because a large flat bow is made in the knot at an end of the traction thread as a coupler 2, it plays the role of the supporting piece 3 instead of a disc shaped plate.

The eardrum perforation patch is packed and sealed in a bag, and sterilized with ethylene dioxide gas, and is reserved for later surgery.

Figure 1:
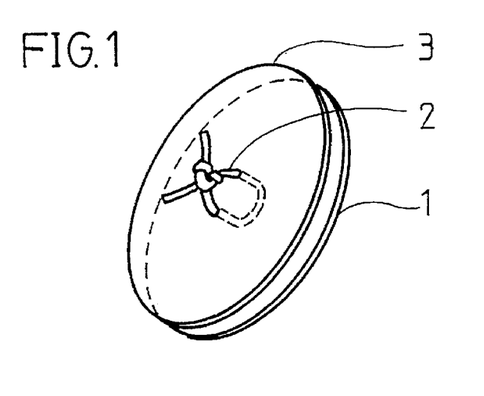
FIG. 1 is a perspective view of a first embodiment of an eardrum perforation patch of the present invention.
Figure 2:
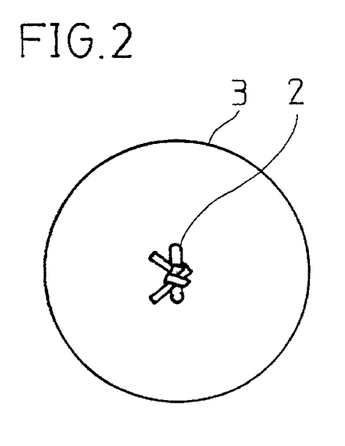
FIG. 2 is a front view of the first embodiment of an eardrum perforation patch of the present invention.
Figure 3:
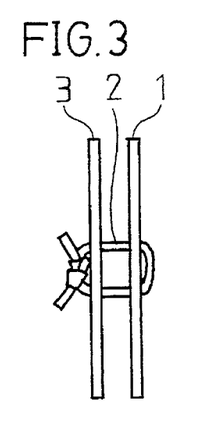
FIG. 3 is a side view of the first embodiment of an eardrum perforation patch of the present invention.
Figure 4:
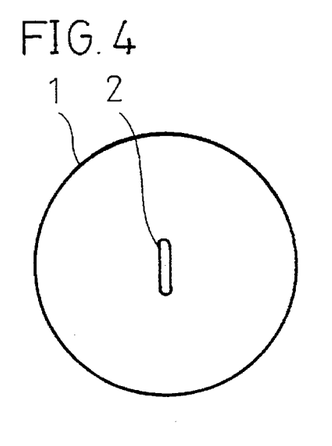
FIG. 4 is a rear view of the first embodiment of an eardrum perforation patch of the present invention.
Figure 5:
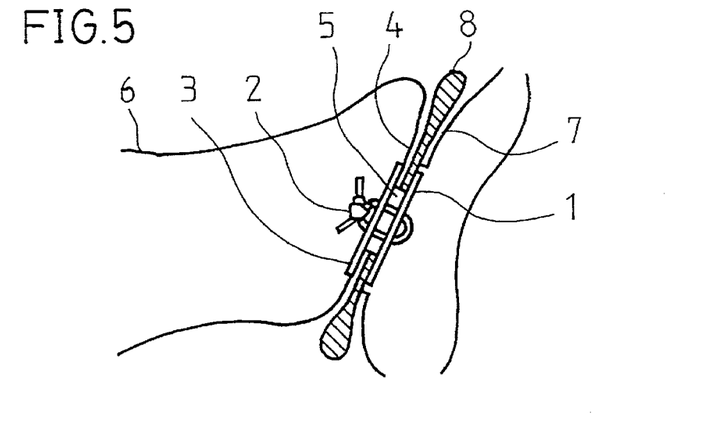
FIG. 5 is a side view of the first embodiment of an eardrum perforation patch of the present invention being held at the perforation of the tympanic membrane shown in cross section.

Turning to FIG. 5, the closure piece 1 is made of absorbable material with affinity for living tissue such that it becomes tissue multiplication ground, and granulation tissue creeps into the voids or gaps in its fiber network from the vascular bed of the lamina propria 8, and grows dissolving and absorbing the network. Capillary vessels will migrate into the closure piece 1 such that it changes into new lamina propria continuing the original one followed by propagation of skin layer outside it and mucosal layer inside it.

The supporting piece 3 keeps the closure piece 3 moist and protects it from drying and permits the growth of the granulation tissue. The supporting piece 3 pulls the closure piece 1 outward and supports the closure piece 1 through the coupler 2. The pair of the closure piece 1 and supporting piece 3 pinches the perforation margin tightly from both inside and outside.

The fastening mechanism is useful for holding the grafted closure piece 1 steady in place and for keeping it in tight contact with the vascular bed around the perforation margin for a long time preventing the closure piece 1 from falling off until the closure piece 1 is organized and changes to a new part of the normal tympanic membrane.

Within a few months the coupler 2 is dissolved and absorbed by creeping granulation tissue, and the supporting piece 3 migrates externally as healing occurs and naturally falls off and forms ear cerumen. The supporting piece 3 can be removed from or can simply fall from the external ear canal 6.

Figure 6:
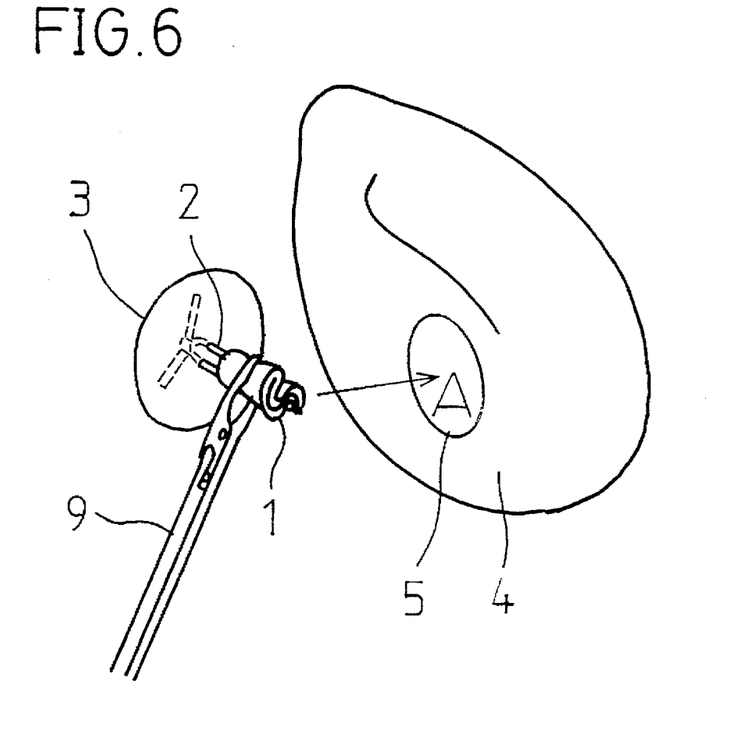
FIG. 6 is a schematic illustration of the first embodiment of an eardrum perforation patch being inserted with a forceps into the tympanic perforation.

An eardrum perforation patch being inserted with forceps 9 into the tympanic perforation is shown in FIG. 6. When applying the patch, the patch is taken out from the sterilized bag and is custom-trimmed for grafting. As shown in FIG. 6, only the closure piece 1 is folded on itself, and is nipped by a pair of forceps 9, and is inserted into the tympanic cavity through the tympanic perforation 5 in the direction of arrow A, and then is released from the forceps 9. After releasing, the closure piece 1 unfolds and returns to its original shape as a disc behind the tympanic membrane because of its elasticity. The supporting piece 3 covers the tympanic membrane. Then the final position of the patch is adjusted.

Figure 7:
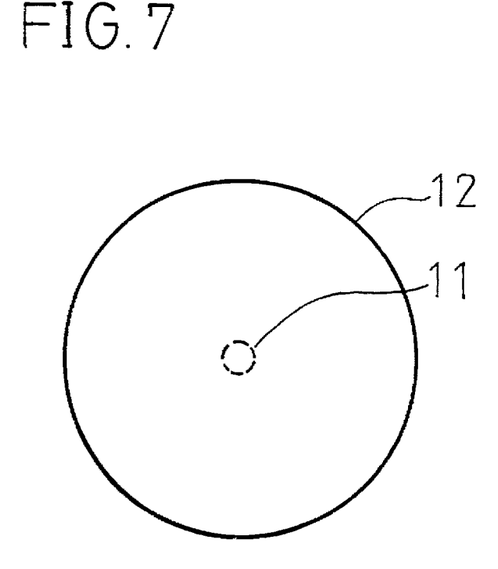
FIG. 7 is a front view of a second embodiment of an eardrum perforation patch of the present invention.
Figure 8:
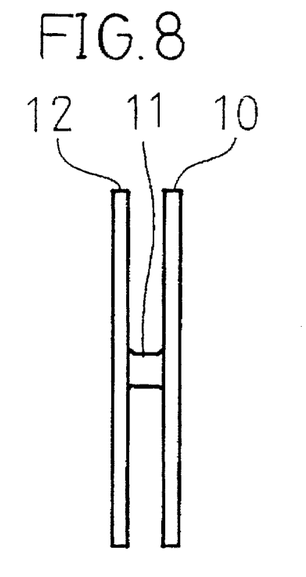
FIG. 8 is a side view of the second embodiment of an eardrum perforation patch of the present invention.

As shown in FIG. 7 and FIG. 8, the eardrum perforation patch of the second embodiment consists of parts of a disc-shaped closure piece 10, a supporting piece 12 and a column-shaped coupled 11. The patch is formed by monoblock molding of absorbable artificial material with biological affinity, for example, collagen fiber. The maneuver to apply the patch is the same as that of the first embodiment of the present invention. The merit is that the patch is made easily by machine production instead of by hand sewing.

Figure 9:
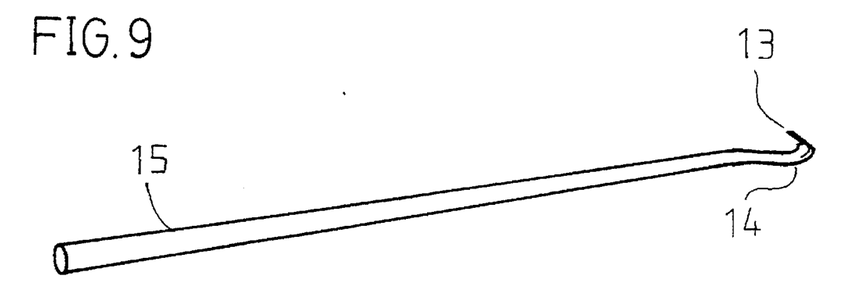
FIG. 9 is a perspective view of a first embodiment of an eardrum undersurface scraper of the present invention.

Next, an eardrum undersurface scraper of the present invention will be described. In FIG. 9 a perspective view of a first embodiment of the eardrum undersurface scraper of the present invention is shown. The eardrum undersurface scraper consists of a head 13 with a blade edge, a neck 14 and a shaft 15. The head 13 with the blade edge is connected to the shaft 15 by the neck 14. The neck 14 is curved and the blade edge is at an angle of more than 90 degrees and less than 360 degrees to the axis of the shaft 15.

Figure 10:
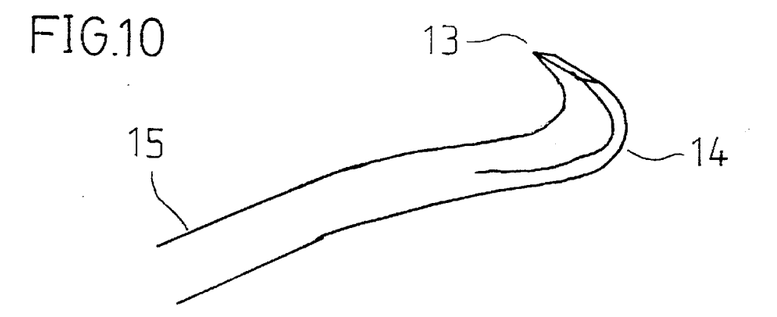
FIG. 10 is a partial enlarged view showing a detail of the head and neck of the first embodiment of an eardrum undersurface scraper of the present invention.

FIG. 10 is a partial enlarged view of the head 13 and the neck 14 of the eardrum undersurface scraper shown in FIG. 9. The width of the blade on head 13 is 1 to 3 mm. and the head 13 is made of cutter stainless steel, and the other parts of the scraper other than the head 13 are made of structural stainless steel.

Figure 11:
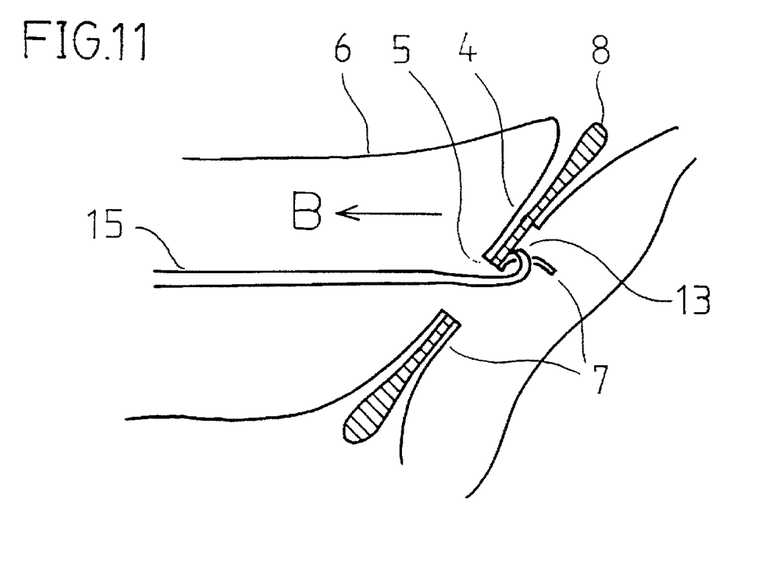
FIG. 11 is a schematic illustration of the first embodiment of an eardrum undersurface scraper of the present invention being applied to the tympanic membrane shown in cross section.

FIG. 11 is a schematic illustration of the first embodiment of the eardrum undersurface scraper of the present invention being applied to the tympanic membrane shown in cross section. Through the tympanic perforation 5 the blade edge of the head 13 is inserted into the space behind the tympanic membrane 4. The curve of the neck 14 permits access for the blade edge of the head 13 to target points on the undersurface, by detouring the free margin of the tympanic perforation 5 and entering into the gap behind the tympanic membrane 4 apart from the perforation margin.

A good view of the undersurface of the entire margin of the perforation 5 and the blade edge of the head 13 are obtained looking through the semitransparent tympanic membrane. After thrusting the blade edge of the head 13 straight into the mucosal layer 7, by stroking it in the direction of arrow B parallel to the tympanic membrane 4, the mucosal layer 7 behind the margin of the tympanic perforation 5 can be surely and easily scraped off and raked out.

The mucosal layer 7, that is, the mucosal barrier on the undersurface of the tympanic membrane 4 is removed for a millimeter or two around the entire circumference of the tympanic perforation 5.

By this procedure, only through the original tympanic perforation 5 vascular network on the lamina propria 8 is the undersurface of the tympanic membrane 4 exposed for a transplantation bed.

Figure 12:
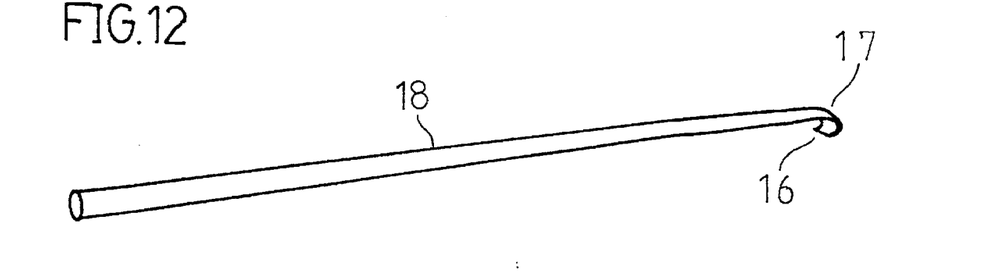
FIG. 12 is a perspective view of a second embodiment of an eardrum undersurface scraper of the present invention.
Figure 13:
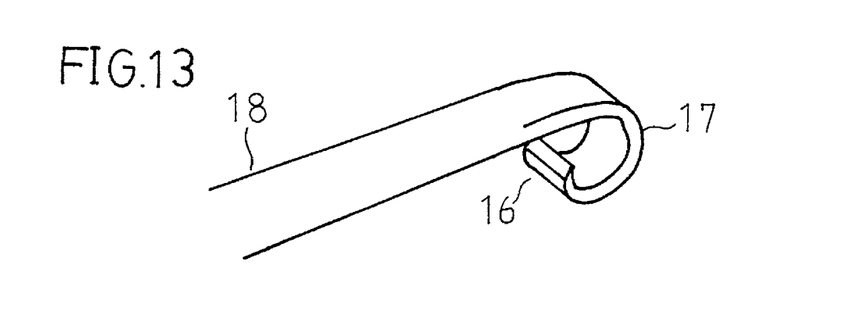
FIG. 13 is a partial enlarged view showing a detail of the head and neck of the second embodiment of an eardrum undersurface scraper of the present invention.

FIGS. 12 and 13 show a second embodiment of an eardrum undersurface scraper of the present invention. An enlarged detail of the head and neck of the eardrum undersurface scraper is shown in FIG. 13. The neck 17 of the eardrum undersurface scraper is curved and the head 16 of the scraper is under the shaft 18, and the blade edge of the head 16 is at an angle of about 270 degrees to the shaft 18.

Figure 14:
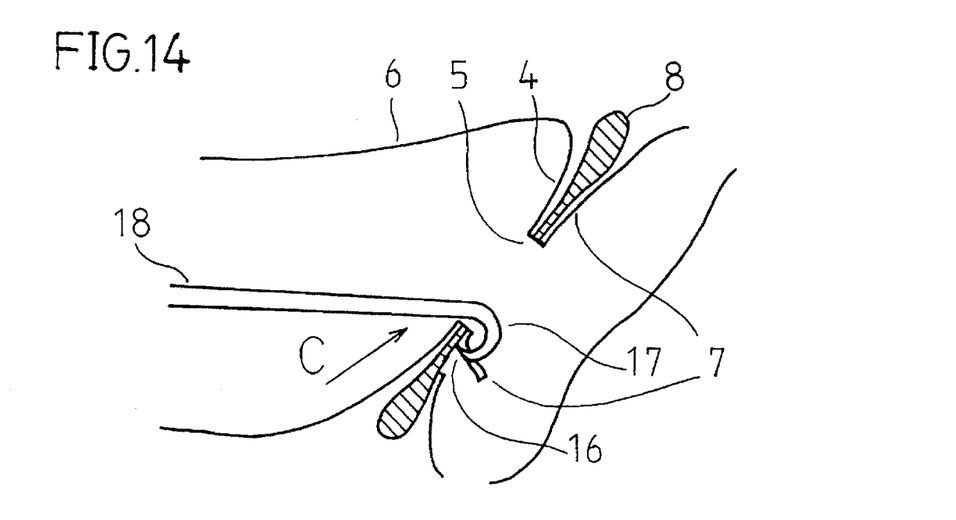
FIG. 14 is a schematic illustration of the second embodiment of an eardrum undersurface scraper of the present invention being applied to the tympanic membrane shown in cross section.

FIG. 14 is a schematic illustration of the second embodiment of the eardrum undersurface scraper of the present invention being applied to the tympanic membrane. The head 16 of the eardrum undersurface scraper reaches the undersurface of the nearer side of the tympanic membrane 4. By pushing the shaft 18 forward, the edge scrapes and rakes the mucosal layer 7 on the undersurface of the tympanic membrane 4.

Figure 15:
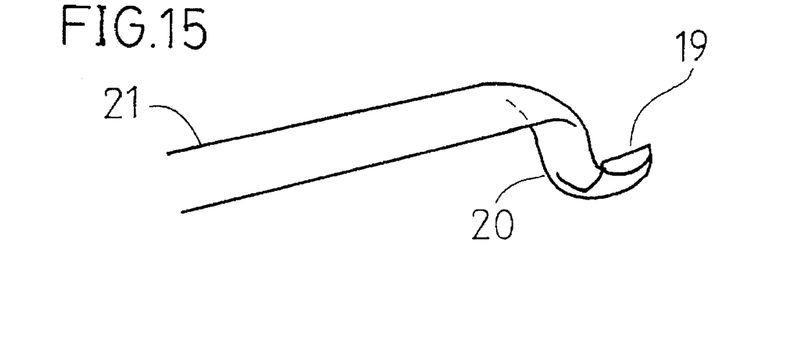
FIG. 15 is a partial enlarged view showing a detail of the head and neck of a third embodiment of an eardrum undersurface scraper of the present invention.

FIG. 15 is a partial enlarged detail of the head and neck of a third embodiment of an eardrum undersurface scraper of the present invention. The undersurface scraper has a curved and twisted neck 20, and a head 19 with a blade edge rotated and deviated laterally from the axis of the shaft 21.

Figure 16:
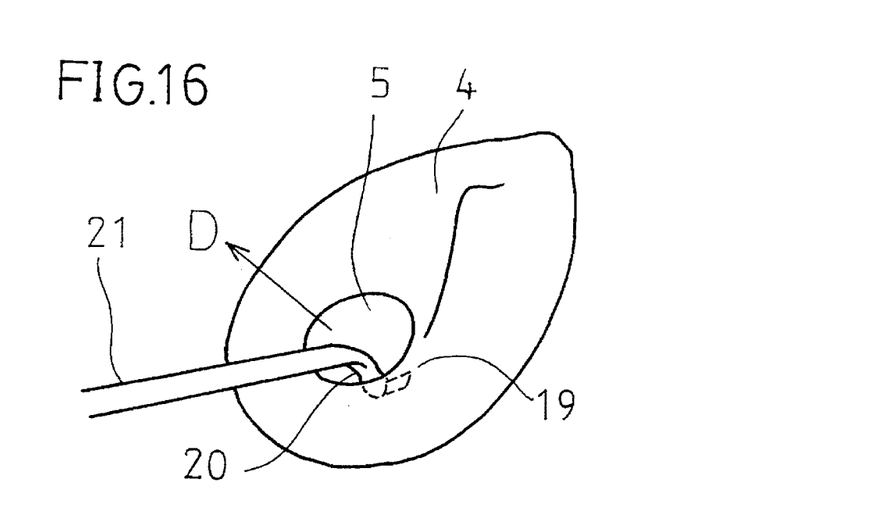
FIG. 16 is a schematic illustration of the third embodiment of an eardrum undersurface scraper of the present invention being applied to the tympanic membrane.

FIG. 16 shows the third embodiment of the eardrum undersurface scraper of the present invention being applied to the tympanic membrane. The blade edge of the head 19 scrapes and rakes out the mucosal layer on the lateral side of the perforation margin by stroking it in the direction of arrow D.

Figure 17:
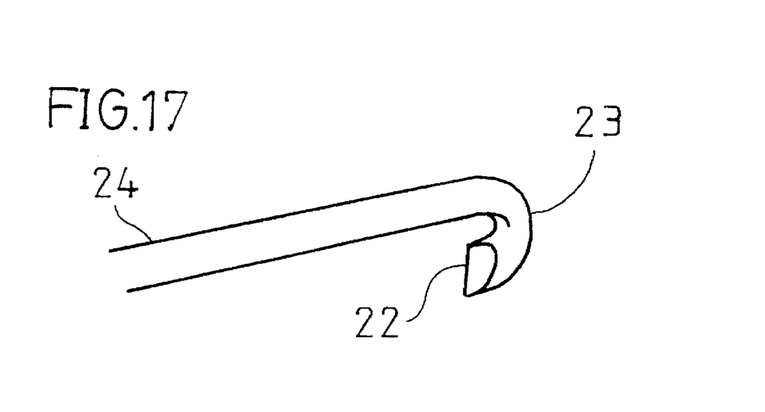
FIG. 17 is a partial enlarged view of a detail of the head and neck of a fourth embodiment of an eardrum undersurface scraper of the present invention.

FIG. 17 shows the head and neck of a fourth embodiment of an eardrum undersurface scraper of the present invention. A head 22 with a blade edge is connected to a neck 23 which is curved and twisted. The blade edge of the head 22 is in the same plane with the axis of a shaft 24 and is at about 180 degrees to the axis.

Figure 18:
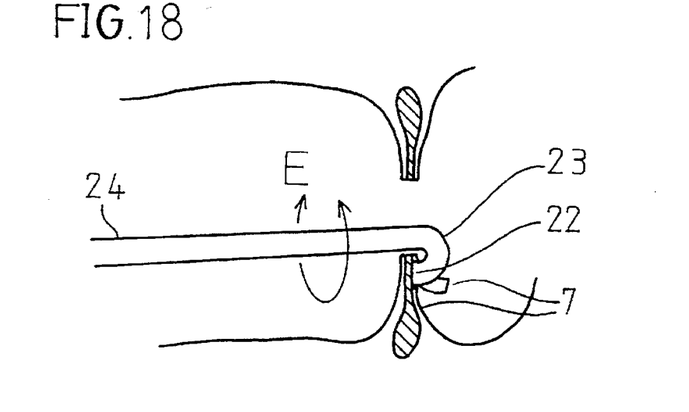
FIG. 18 is a schematic illustration of the head and neck of the fourth embodiment of an eardrum undersurface scraper of the present invention being applied to the tympanic membrane shown in cross section.

FIG. 18 illustrates the head and neck of the fourth embodiment of an eardrum undersurface scraper of the present invention being applied to the tympanic membrane. The blade edge of the head 22 is thrusted straight into the mucosal layer 7 on the undersurface of the tympanic membrane and is moved in the tangential direction of arrow E.

In actual surgery, an assortment of the scrapers including from the first to the fourth embodiment can be used in order to extend scraping mucosal layer 7 on the undersurface around the tympanic perforation 5 in all directions.

Figure 19:
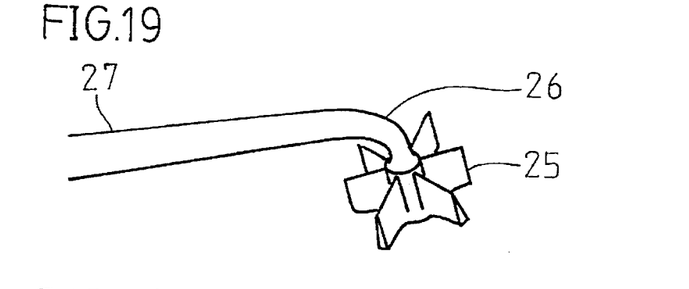
FIG. 19 is a partial enlarged view of a detail of the head and neck of a fifth embodiment of an eardrum undersurface scraper of the present invention.

FIG. 19 is an enlarged detail of the head and neck of a fifth embodiment of an eardrum undersurface scraper of the present invention. The head 25 has blade edges radially arranged from the axis of the neck 26 on shaft 27. With this scraper, the undersurface in all of the circumferential margin of the tympanic perforation can evenly be scraped.

Figure 20:
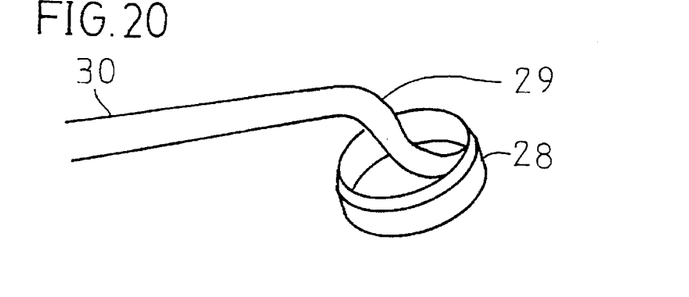
FIG. 20 is a partial enlarged view of a detail of the head and neck of a sixth embodiment of an eardrum undersurface scraper of the present invention.

FIG. 20 is an enlarged detail of the head and neck of a sixth embodiment of an eardrum undersurface scraper of the present invention. The head 28 of the scraper has a circular blade edge on a circular belt. Head 28 is connected to shaft 30 by the neck 29. This scraper scrapes all the circumferential margin and yields a smooth surface of a grafting bed.

Figure 21:
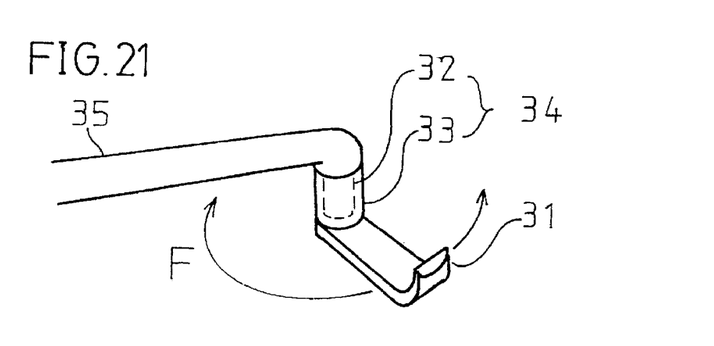
FIG. 21 is a partial enlarged view of a detail of the head and neck of a seventh embodiment of an eardrum undersurface scraper of the present invention.

FIG. 21 is a partial enlarged view showing a detail of the head and neck of a seventh embodiment of an eardrum undersurface scraper of the present invention. This scraper has a neck 34 which consists of a pin 32 and socket 33. The head 31 can be turned and its direction to the shaft 35 is variable. This scraper scrapes the undersurface in all the circumferential margin of the tympanic perforation.

The present invention is valuable as a material and a surgical tool for tympanic perforation repair, and its sure pinching mechanism, easy surgical maneuvering, and minimum harm provide a convenient operation and high success rate. It is useful in such fields as tympanic perforation repair for restoration of hearing function and curing ear discharge.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. An eardrum undersurface scraper comprising:

a shaft having a longitudinal axis;

a head with at least one blade edge thereon, the blade edge being at an angle of more than 90 degrees and less than 360 degrees to the shaft, the head scraping mucosa upon insertion through a perforation in a tympanic membrane and manipulation of the scraper; and a neck connecting the head with the shaft, the neck being curved;

said at least one blade removes mucosa on an undersurface of the tympanic membrane through the tympanic perforation in the tympanic membrane to form a grafting bed on the tympanic membrane.

2. The eardrum undersurface scraper as claimed in claim 1, wherein the neck generally has a c-shape and wherein the blade edge of the head overlies and is spaced from an end of the shaft.

3. The eardrum undersurface scraper as claimed in claim 1, wherein said neck is twisted and said head with the blade edge is rotated and deviated laterally from a longitudinal axis of the shaft.

4. The eardrum undersurface scraper as claimed in claim 1, wherein said neck is twisted and said blade edge is in a same plane with a longitudinal axis of the shaft.

5. The eardrum undersurface scraper as claimed in claim 1, wherein an end of the shaft has a flat upper surface and wherein said neck is twisted and said blade edge is in a plane which is parallel to a plane in which the flat upper surface of the end of the shaft is located.

6. The eardrum undersurface scraper as claimed in claim 1, wherein the neck is curved and a plurality of blade edges are provided, the blade edges being arranged radially extending from the neck.

7. The eardrum undersurface scraper as claimed in claim 1, wherein the head and the blade edge are circular, the head being a circular belt and the blade edge being on one side of the head.

8. The eardrum undersurface scraper as claimed in claim 1, wherein the neck comprises a pin and a socket, the head being pivotable on the neck.

9. The eardrum undersurface scraper as claimed in claim 8, wherein the head is rotatable 360 degrees about the neck and wherein the blade edge on the head is rotatable in a plane which is parallel to a longitudinal axis of the shaft.

* * * * *